(12) United States Patent
Sandford

(10) Patent No.: US 9,176,047 B2
(45) Date of Patent: *Nov. 3, 2015

(54) CITRATE DETECTOR FOR BLOOD PROCESSING SYSTEM

(71) Applicant: Fenwal, Inc., Lake Zurich, IL (US)

(72) Inventor: Craig Sandford, Buffalo Grove, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,526

(22) Filed: Jun. 17, 2014

(65) Prior Publication Data

US 2014/0291535 A1 Oct. 2, 2014

Related U.S. Application Data

(63) Continuation of application No. 13/752,457, filed on Jan. 29, 2013, now Pat. No. 8,803,090.

(60) Provisional application No. 61/724,571, filed on Nov. 9, 2012.

(51) Int. Cl.
*G01J 5/00* (2006.01)
*G01N 21/17* (2006.01)
(Continued)

(52) U.S. Cl.
CPC ............. *G01N 21/17* (2013.01); *A61M 1/367* (2013.01); *A61M 1/3621* (2013.01); *A61M 5/00* (2013.01); *G01N 33/49* (2013.01); *A61M 1/0209* (2013.01); *A61M 1/16* (2013.01); *A61M 1/342* (2013.01); *A61M 1/3672* (2013.01);
(Continued)

(58) Field of Classification Search
CPC .............................. G01N 21/17; G01N 33/49
See application file for complete search history.

(56) References Cited

U.S. PATENT DOCUMENTS 4,501,531 A * 2/1985 Bilstad et al. .................. 417/63
4,648,866 A * 3/1987 Malbrancq et al. .......... 604/6.05
(Continued)

FOREIGN PATENT DOCUMENTS

WO    WO 95/03112 A1    2/1995
WO    WO 2007/101064 A2    9/2007

OTHER PUBLICATIONS

Tsimbler et al., "The IR absorption spectra of the tartrate and citrate complexes of nickel, cobalt and iron," Sep. 1969, (Translated from Zhurnal Prikladnoi Spektroskopii, vol. 11, No. 3, pp. 533-528), pp. 1096-1101.*

(Continued)

Primary Examiner — Kiho Kim
(74) Attorney, Agent, or Firm — Cook Alex Ltd.

(57) ABSTRACT

A citrate detector is provided for use in combination with a blood processing system and replacement fluid tubing or conduit of a disposable set. The citrate detector comprises a light source and a light detector. The light source is configured to emit a light having a wavelength absorbed by citrate, but at least partially transmitted by the replacement fluid conduit of the disposable set. The light detector is configured to receive at least a portion of the light from the light source and generate a signal indicative of the presence or absence of citrate in the replacement fluid conduit based, at least in part, on the amount of light received from the light source. A blood processing system incorporating such a citrate detector may include a flow detector for determining whether fluid is present in the conduit prior to checking for the presence of citrate.

21 Claims, 6 Drawing Sheets

(51) Int. Cl.
    *A61M 1/36*     (2006.01)
    *G01N 33/49*     (2006.01)
    *A61M 5/00*     (2006.01)
    *A61M 1/02*     (2006.01)
    *A61M 1/16*     (2006.01)
    *A61M 1/34*     (2006.01)

(52) U.S. Cl.
    CPC ......... *A61M 1/3693* (2013.01); *A61M 2205/18* (2013.01); *A61M 2205/3306* (2013.01); *A61M 2205/3313* (2013.01)

(56) References Cited

U.S. PATENT DOCUMENTS

| | | | |
|---|---|---|---|
| 4,687,580 | A | 8/1987 | Malbrancq et al. |
| 4,851,126 | A | 7/1989 | Schoendorfer |
| 5,370,802 | A | 12/1994 | Brown |
| 5,649,903 | A | 7/1997 | Deniega |
| 5,713,351 | A * | 2/1998 | Billings et al. ............... 600/309 |
| 5,868,696 | A | 2/1999 | Giesler |
| 5,993,370 | A | 11/1999 | Brown |
| 6,348,156 | B1 | 2/2002 | Vishnoi |
| 6,558,307 | B2 | 5/2003 | Headley |
| 6,582,349 | B1 | 6/2003 | Cantu |
| 6,773,413 | B2 | 8/2004 | Keller |
| 7,011,761 | B2 | 3/2006 | Muller |
| 7,087,177 | B2 | 8/2006 | Min |
| 7,297,272 | B2 | 11/2007 | Min |
| 7,354,415 | B2 | 4/2008 | Bainbridge et al. |
| 7,438,679 | B2 | 10/2008 | Hlavinka et al. |
| 7,442,178 | B2 | 10/2008 | Chammas |
| 7,452,322 | B2 | 11/2008 | Headley et al. |
| 7,473,216 | B2 | 1/2009 | Lolachi et al. |
| 7,497,944 | B2 | 3/2009 | Hogberg et al. |
| 7,582,049 | B2 | 9/2009 | Hlavinka et al. |
| 7,588,692 | B2 | 9/2009 | Antwiler et al. |
| 7,648,452 | B2 | 1/2010 | Holmes et al. |
| 7,648,639 | B2 | 1/2010 | Holmes et al. |
| 7,674,221 | B2 | 3/2010 | Hudock et al. |
| 7,686,779 | B1 | 3/2010 | Gibbs |
| 7,756,657 | B2 | 7/2010 | Davidson et al. |
| 7,766,809 | B2 | 8/2010 | Dolecek et al. |
| 7,811,463 | B2 | 10/2010 | Dolecek et al. |
| 7,819,793 | B2 | 10/2010 | Lindell et al. |
| 7,833,185 | B2 | 11/2010 | Felt et al. |
| 7,867,159 | B2 | 1/2011 | Dolecek et al. |
| 7,934,603 | B2 | 5/2011 | Eaton et al. |
| 7,943,916 | B2 | 5/2011 | Carter et al. |
| 7,963,901 | B2 | 6/2011 | Langley et al. |
| 7,981,019 | B2 | 7/2011 | Holmes et al. |
| 8,057,377 | B2 | 11/2011 | Holmes et al. |
| 8,075,468 | B2 | 12/2011 | Min |
| 2001/0007022 | A1 * | 7/2001 | Althaus et al. ........... 530/388.24 |
| 2003/0049850 | A1 * | 3/2003 | Golden ........................ 436/56 |
| 2003/0066807 | A1 | 4/2003 | Suzuki |
| 2007/0066928 | A1 | 3/2007 | Lannoy |
| 2008/0147240 | A1 | 6/2008 | Hudock et al. |
| 2008/0149564 | A1 | 6/2008 | Holmes |
| 2008/0171646 | A1 | 7/2008 | Dolecek et al. |
| 2008/0248938 | A1 | 10/2008 | Chammas |
| 2008/0283473 | A1 | 11/2008 | Holmes et al. |
| 2009/0018418 | A1 | 1/2009 | Markle et al. |
| 2009/0221948 | A1 * | 9/2009 | Szamosfalvi et al. ....... 604/6.07 |
| 2009/0259162 | A1 | 10/2009 | Ohashi et al. |
| 2009/0272701 | A1 | 11/2009 | Holmes et al. |
| 2009/0286221 | A1 | 11/2009 | Klip et al. |
| 2009/0298665 | A1 | 12/2009 | Dolecek et al. |
| 2009/0317305 | A1 | 12/2009 | Hudock et al. |
| 2010/0026986 | A1 | 2/2010 | Stanton et al. |
| 2010/0081196 | A1 | 4/2010 | Felt et al. |
| 2010/0082011 | A1 | 4/2010 | Lewis et al. |
| 2010/0210441 | A1 | 8/2010 | Dolecek |
| 2010/0267538 | A1 | 10/2010 | Green et al. |
| 2010/0273627 | A1 | 10/2010 | Hudock et al. |
| 2011/0001422 | A1 * | 1/2011 | Aanegola et al. ............. 313/501 |
| 2011/0003675 | A1 | 1/2011 | Dolecek |
| 2011/0028295 | A1 | 2/2011 | Menhennett et al. |
| 2011/0059834 | A1 | 3/2011 | Eberle |
| 2011/0077140 | A1 | 3/2011 | Holmes et al. |
| 2011/0136646 | A1 | 6/2011 | Pearce et al. |
| 2011/0136650 | A1 | 6/2011 | Ellingboe et al. |
| 2011/0178453 | A1 | 7/2011 | Pages et al. |
| 2011/0224064 | A1 | 9/2011 | Pittinger et al. |
| 2012/0098559 | A1 * | 4/2012 | Bolt et al. ................. 324/754.03 |
| 2014/0132945 | A1 | 5/2014 | Sandford |

OTHER PUBLICATIONS

Rajos et al., "Use of experimental design for calibration and validation of ascorbic acid and citric acid mixtures," 2008, Journal of Mexican Chemical Society, vol. 52 No. 4, pp. 229-234.*

Lopez et al., "Simultaneous determination of the major organic acids, sugars, glycerol, and ethanol by HPLC in grape musts and white wines," 1996, Journal of Chromatographic Science, vol. 34, pp. 254-257.*

Extended European Search Report for European Patent Application No. EP 13164919.6, dated Dec. 6, 2013.

Nagali et al., "Design of a diode-laser sensor to monitor water vapor in high-pressure combustion gases," 1997, Applied Optics, vol. 36, No. 36, pp. 9518-9527.

* cited by examiner

CITRATE DETECTOR FOR BLOOD PROCESSING SYSTEM

CROSS-REFERENCE TO RELATED APPLICATIONS

This application is a continuation of U.S. non-provisional patent application Ser. No. 13/752,457, filed on Jan. 29, 2013, which claims the benefit of U.S. provisional patent application Ser. No. 61/724,571, filed on Nov. 9, 2012, both of which are incorporated herein by reference.

BACKGROUND

1. Field of the Disclosure

The disclosure relates to blood treatment systems and methods. More particularly, the disclosure relates to systems and methods for optically detecting or monitoring characteristics of fluid (e.g., the presence of citrate) within a blood processing device.

2. Description of Related Art

Various blood processing systems now make it possible to collect particular blood constituents, instead of whole blood, from a blood source. Typically, in such systems, whole blood is drawn from a blood source, the particular blood component or constituent is separated, removed, and collected, and the remaining blood constituents are returned to the blood source. Removing only particular constituents is particularly advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood may be separated into its constituents through any of a number of automated procedures, such as centrifugation, membrane separation, and others. Centrifugation, for example, requires that the whole blood be passed through a centrifuge after it is withdrawn from, and before it is returned to, the blood source. To reduce contamination and possible infection (if the blood source is a human donor or patient), the blood is preferably processed within a sealed, sterile fluid flow system during the centrifugation process. Typical blood processing systems include a disposable, sealed, and sterile flow circuit, including a centrifuge chamber portion, that is mounted in cooperation on a durable, reusable assembly containing the hardware (centrifuge, drive system, pumps, valve actuators, programmable controller, and the like) that rotates a centrifuge chamber and controls the flow through the fluid circuit.

In some cases, the disposable flow circuit is configured to allow attachment of additional components, such as bags containing fluids used during the procedure. These fluids may be used for different purposes, such as anticoagulant fluid for preventing the coagulation of blood outside of the body, storage fluid to be added to separated blood components for long-term storage, and replacement fluid to be infused into a patient or donor to replace blood components that are being stored for later use. Some fluids that are used for one purpose may be harmful if used for a different purpose. For example, sodium citrate is commonly used as an anticoagulant, but the excess infusion of sodium citrate into a patient or donor may be potentially harmful by overly increasing the citrate concentration of the blood. Accordingly, care must be taken to ensure that the proper fluid containers are connected to the various ports or access points of a disposable flow circuit.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a citrate detector is provided for use in combination with a blood processing system and a replacement fluid flow conduit of a disposable fluid circuit or set. The citrate detector comprises a light source and a light detector. The light source is configured to emit a light having a wavelength absorbed by citrate, but at least partially transmitted by the replacement fluid flow conduit of the disposable set. The light detector is configured to receive at least a portion of the light from the light source and generate a signal indicative of the presence or absence of citrate in the replacement fluid flow conduit based, at least in part, on the amount of light received from the light source.

In another aspect, a blood processing system is provided for use in combination with a replacement fluid flow conduit of a disposable set. The blood processing system includes a citrate detector and a controller. The citrate detector comprises a light source and a light detector. The light source is configured to emit a light having a wavelength absorbed by citrate, but at least partially transmitted by the replacement fluid flow conduit of the disposable set. The light detector is configured to receive at least a portion of the light from the light source and generate a signal indicative of the presence or absence of citrate between the light source and the light detector based, at least in part, on the amount of light received from the light source. The controller is configured to receive the signal from the light detector and determine whether citrate is present between the light source and the light detector based, at least in part, on the signal. The controller may generate audible and/or visual warnings depending on the signal and may control the centrifuge apparatus by flow control or other operation functions to limit adverse consequences.

In yet another aspect, a method is provided for monitoring fluid within a blood processing system having a replacement fluid flow conduit. The method includes directing light into the replacement fluid flow conduit, with the light having a wavelength absorbed by citrate, but at least partially transmitted by the replacement fluid flow conduit. Light exiting or reflected by the replacement fluid flow conduit is detected and it is determined whether citrate is present in the replacement fluid flow conduit based, at least in part, on the light exiting the replacement fluid flow conduit.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
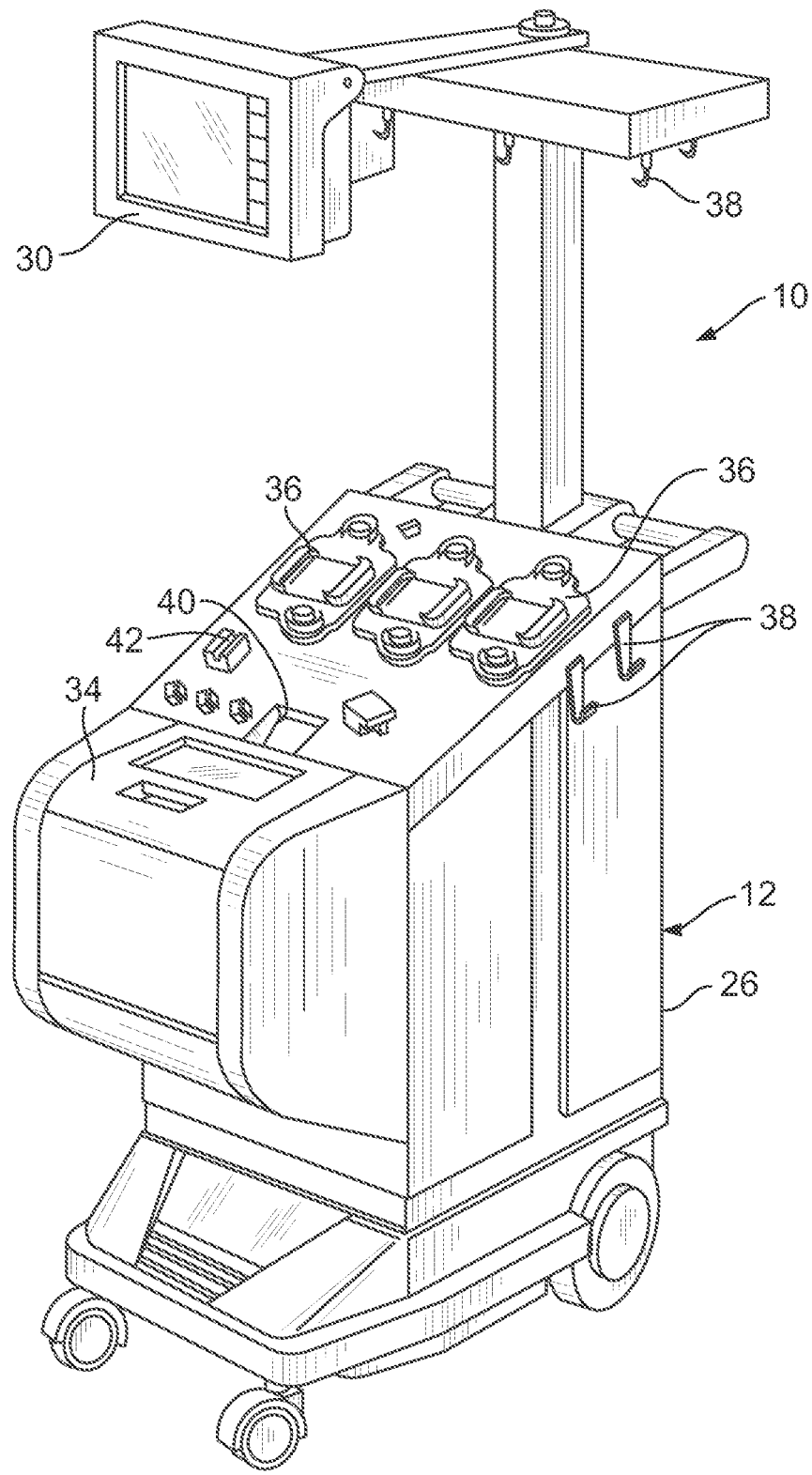
FIG. 1 is a perspective view of an exemplary durable blood processing system that may be used in combination with citrate detectors according to the present disclosure.

FIG. 1 shows a centrifugal blood processing system 10. The system is currently marketed as the AMICUS® separator by Fenwal, Inc. of Lake Zurich, Ill. The system 10 can be used for processing various fluids, but is particularly well suited for processing whole blood, blood components, or other suspensions of biological cellular materials. The system 10 includes a centrifuge assembly 12 for separating a fluid into its constituent parts. A more detailed description of the centrifuge assembly 12 and the other elements of the system 10 can be found in U.S. Pat. No. 5,996,634, which is incorporated by reference herein. While FIG. 1 illustrates a centrifugal blood processing system, it should be understood that the illustrated system is merely exemplary, and other blood processing systems (including filter- or membrane-based blood separators and other centrifugation or other separation systems) may be used in combination with citrate detectors according to the present disclosure.

When used for processing blood, a blood component, or any other body fluid, devices and methods according to the present disclosure may be used with any suitable fluid source. For example, the fluid source may be a living human or non-human animal whose bodily fluid is directly drawn into the device for processing. In other embodiments, the fluid to be processed does not come directly from a living human or non-human animal, but is instead provided directly from a non-living source, such as a container holding an amount of fresh or stored fluid (e.g., blood or a blood component that has been previously drawn from a living source and stored). In additional embodiments, there may be a plurality of fluid sources, which may all be living sources or non-living sources or a combination of living and non-living sources.

Figure 2:
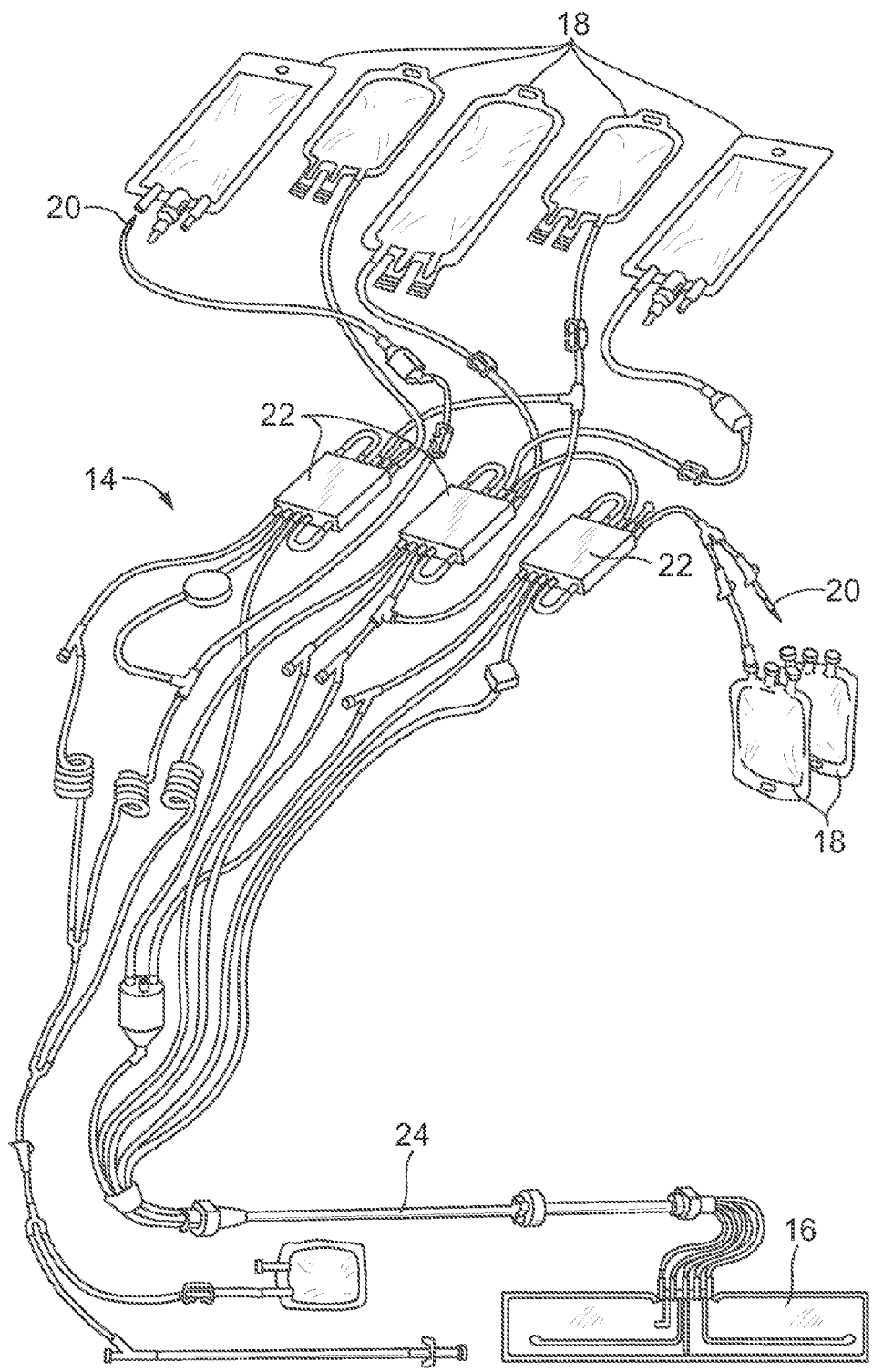
FIG. 2 is a perspective view of a disposable set usable in association with the durable fluid processing system of FIG. 1.
Figure 3:
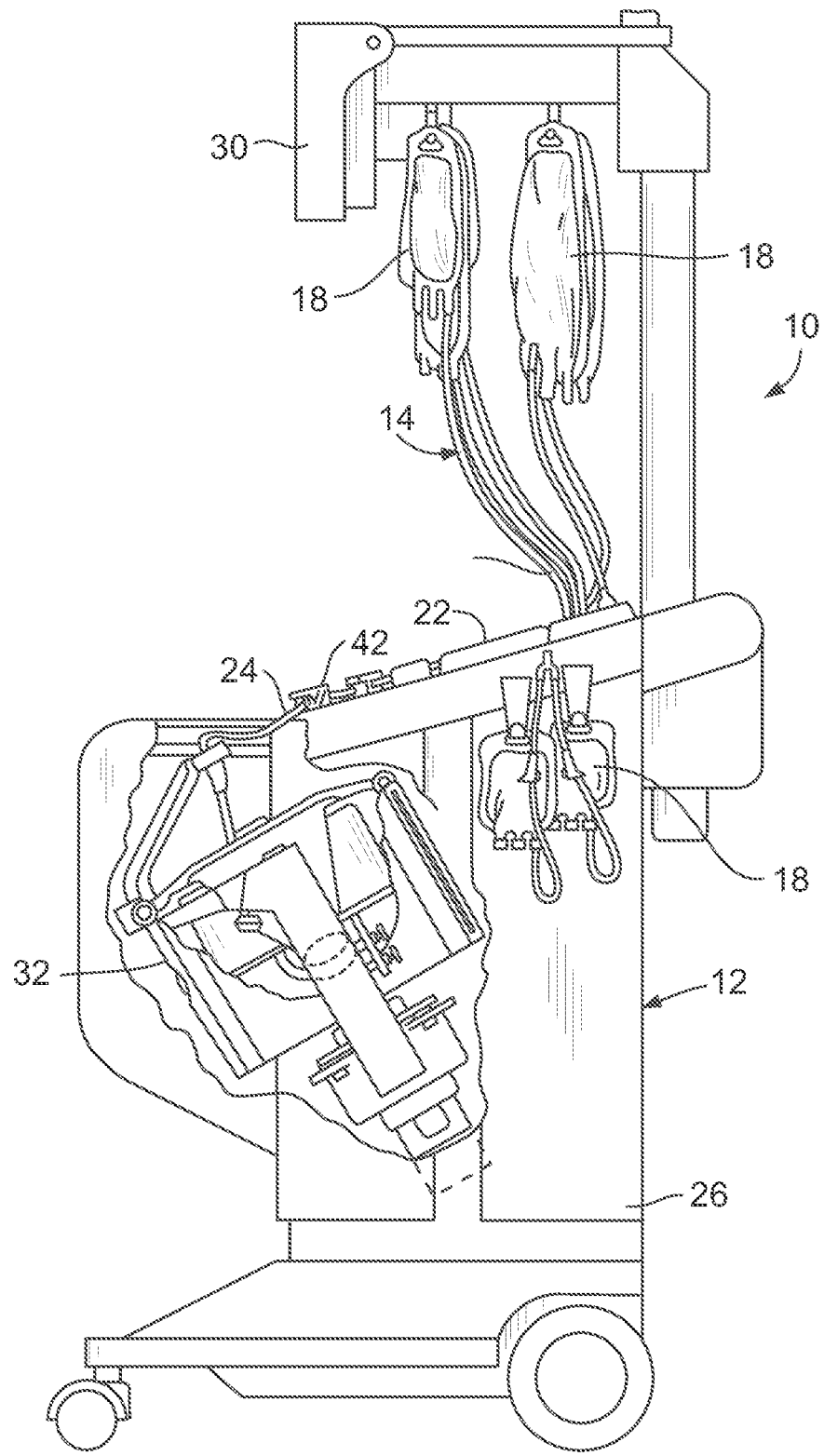
FIG. 3 is a side elevational view of the disposable set of FIG. 2 mounted on the durable blood processing system of FIG. 1, which is partially broken away.

The durable blood processing system 10 is used in combination with a disposable processing set 14, an example of which is shown in FIG. 2. FIG. 3 shows the disposable set 14 mounted on the durable system 10. The disposable set 14 is a preferably single use, disposable item loaded on the system 10 at the time of use. After a fluid processing procedure has been completed, the operator preferably removes the disposable set 14 from the system 10 and discards it. It should be understood that the illustrated disposable set 14 of FIG. 2 is merely exemplary. The illustrated disposable set 14 is suitable for use with a system 10 as shown in FIG. 1, but those of ordinary skill in the art will appreciate that differently configured disposable sets are appropriate for use with different blood processing systems.

The disposable set 14 includes a processing chamber 16 (FIG. 2). In use, the centrifuge assembly 12 rotates the processing chamber 16 to centrifugally separate blood components. Whole blood is conveyed to the processing chamber 16, and separated blood components are conveyed from the processing chamber 16, through a plurality of flexible tubes that form part of a fluid circuit. The fluid circuit further includes a plurality of containers 18 that may be supported by elevated hangers located over the centrifuge assembly 12 (see FIG. 3) and that dispense and receive liquids during processing. At least some of the containers 18 are separate from the disposable set 14 and connected thereto by connectors 20. The nature of the connectors 20 may vary without departing from the scope of the present disclosure. For example, the connectors 20 may be cannulas configured to puncture the containers 18 to establish fluid communication between the fluid circuit and the containers 18. Other connectors and means for connecting separate containers to a disposable set 14, such as sterile connection devices, are known to those of ordinary skill in the art and may be employed without departing from the scope of the present disclosure. Preferably, the disposable set 14 is a pre-assembled closed system, with the connectors 20 allowing for sterile connection of the containers 18 to the fluid circuit.

Fluid flow through the fluid circuit 14 may be controlled in a variety of ways. In one embodiment, fluid flow is controlled via cassettes 22 with pre-formed fluid passageways, which may be selectively opened and closed pneumatically, hydraulically, or by movable actuators. The number of cassettes may vary, but in the illustrated embodiment, there are three cassettes 22, which operate in association with valve and pump stations on the centrifuge assembly 12 to direct liquid flow among multiple liquid sources and destinations during a blood processing procedure. Tubes connected to the processing chamber 16 lead to a flexible umbilicus 24, with additional tubes at the other end of the umbilicus 24 fluidly connecting the processing chamber 16 (via the umbilicus 24) to the remainder of the disposable set 14, including the containers 18 and the cassettes 22.

As illustrated, the centrifuge assembly 12 includes a wheeled cabinet 26 that can be easily rolled from place to place. A user-actuable processing controller 30 is provided which enables the operator to control various aspects of the blood processing procedure. A centrifuge rotor assembly 32 is provided behind a fold-open door 34 (FIG. 1) that can be pulled open at the front of the cabinet 26. A plurality of valve and pump stations 36 (FIG. 1) are provided on the top face of the cabinet for receiving and controlling the various cassettes 22. A plurality of hooks or hangers 38 are provided on the cabinet 26 for suspending the various containers 18.

Figure 4:
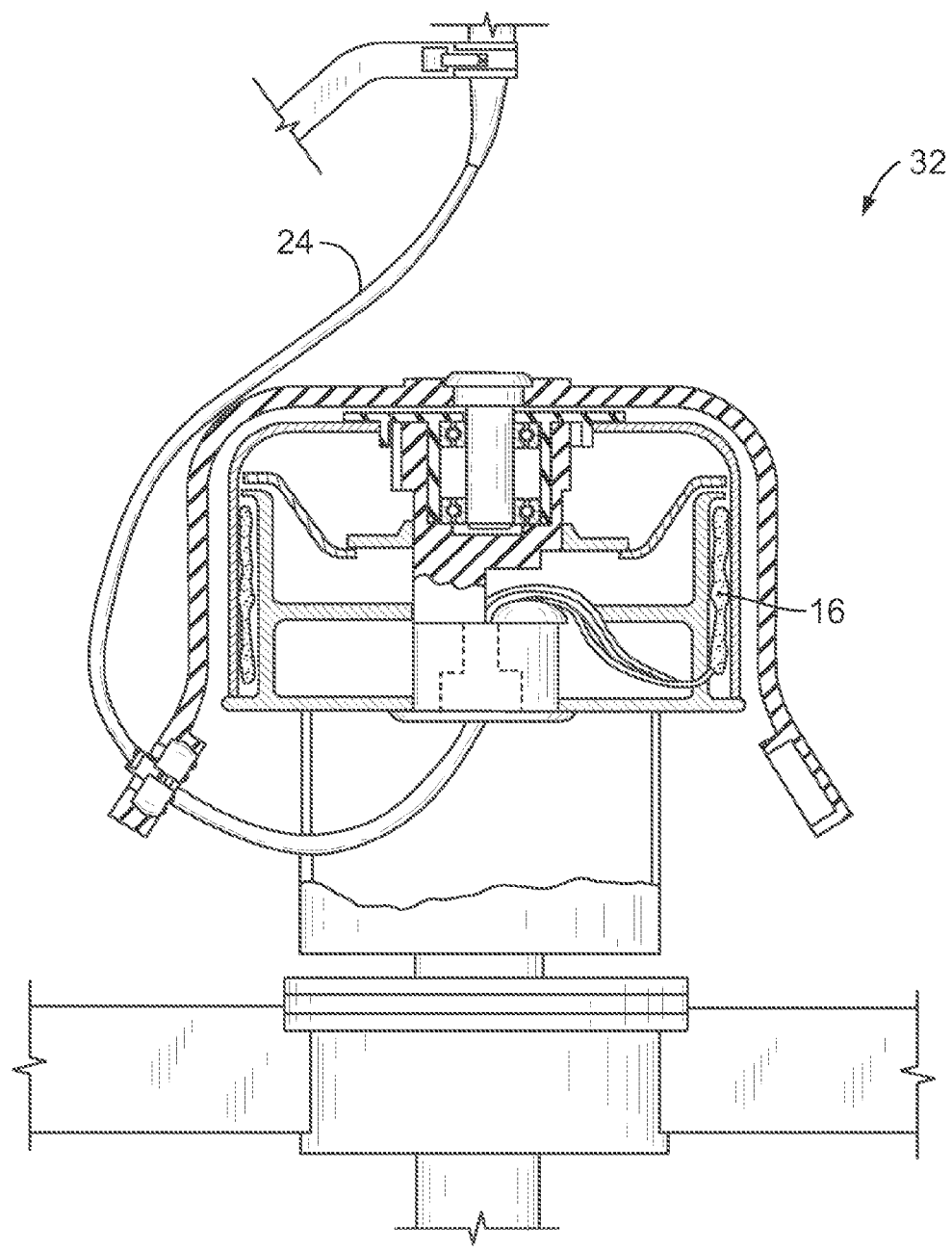
FIG. 4 is a side detail view of a centrifuge included in the durable blood processing system of FIG. 1, showing the centrifuge in combination with an umbilicus of the disposable set.

In use, the fold open door 34 is opened and the processing chamber 16 of the disposable set 14 is mounted in the centrifuge rotor assembly 32 (FIG. 4). The umbilicus 24 is threaded through the centrifuge rotor assembly 32 and out through an opening 40 in the upper panel of the cabinet 26 (FIG. 3). The cassettes 22 are snapped into respective ones of the valve and pump stations 36 and the containers 18 are hung from the appropriate hangers 38 (FIG. 3). After appropriate connections are made to the patient or donor using known intravenous techniques, the operator enters appropriate commands on the processing controller 30 to begin the desired processing procedure.

In an exemplary processing procedure, whole blood or a fluid containing one or more blood components is drawn into the disposable set 14 by a phlebotomy needle or other access device. To reduce clotting, anticoagulant is added to the fluid from one of the containers 18. The anticoagulated blood flows into the processing chamber 16, where it is separated into at least two components based on their relative densities (e.g., a relatively high density component, such as red blood cells, and a relatively low density component, such as platelet-rich plasma). One of the components (the high density component in one embodiment) may be pumped out of the processing chamber 16 and into one of the container 18, which serves as a storage container. The storage container may be provided with an amount of storage fluid or, alternatively, storage fluid may be added to the storage container from one of the other containers 18. The other component (the low density component in one embodiment) may be pumped out of the processing chamber 16 and returned to the blood source. Replacement fluid, such as saline, may be added to the fluid that is returned to the blood source to compensate for the blood volume deficit caused by storage of the selected blood component(s) in the storage container after separation. Other blood processing protocol may be carried out using the system 10 and disposable set 14 (e.g., procedures in which one of the separated components is further fractionated to form two or more sub-components), and it should be understood that the foregoing procedure is merely exemplary, rather than limiting.

Figure 5:
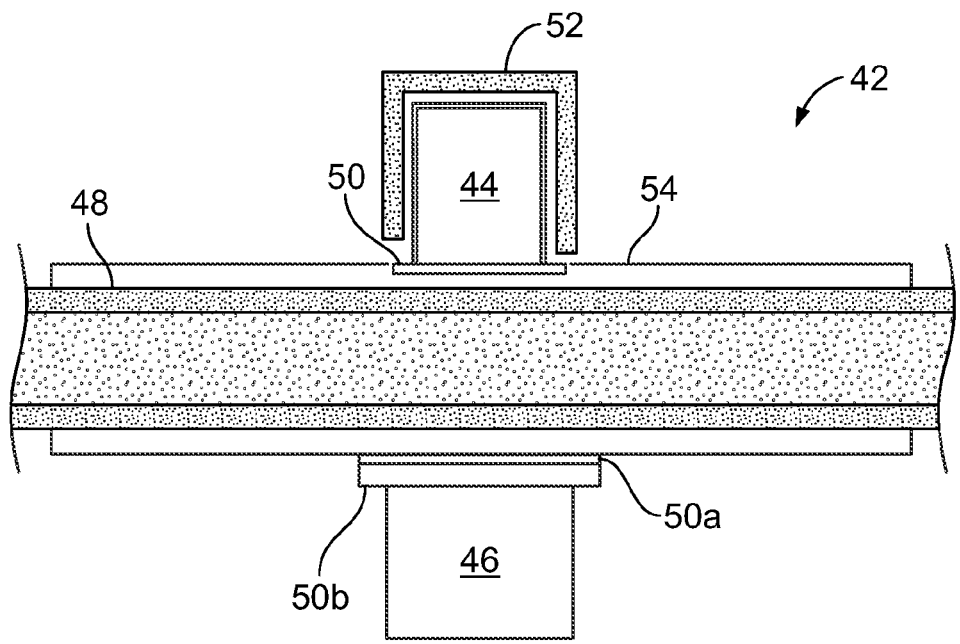
FIG. 5 is a diagrammatic view of a citrate detector that may be used in combination with the blood processing system and disposable set of FIG. 3.

To better ensure that the separate containers 18 are properly connected to the remainder of the disposable set 14 and to protect a donor or patient from overexposure to citrate, which is a common component of commercial anticoagulants, the system 10 may be provided with a citrate detector 42 (FIGS. 1 and 5). The citrate detector 42 includes a light source 44 (such as, but not limited to, one or more light-emitting diodes) and a light detector 46 (such as, but not limited to, a photodiode), with the light detector 46 being configured and oriented to receive light from the light source 44. The light source 44 and light detector 46 are spaced apart a sufficient distance to accommodate a conduit or length of tubing 48 therebetween. The conduit 48 is at least a portion or segment of the means by which replacement fluid is intended to flow from the appropriate container 18 into the disposable set 14. FIG. 1 illustrates the citrate detector 42 as being associated with the top face of the cabinet 26, but may be located anywhere else appropriate to accommodate the replacement fluid conduit 48.

The light source 44 emits a light having a wavelength that is absorbed at a higher level by citrate than by another fluid, e.g., replacement fluid (such as saline or another sodium chloride mixture) or by the conduit 48. Preferably, the light emitted by the light source 44 has a wavelength that is substantially transmitted through the replacement fluid and the conduit 48, with little to no absorption of the light. It has been found that ultraviolet light in the range of approximately 200 to 250 nm is absorbed by citrate or a citrate solution, but is substantially transmitted by or absorbed at a significantly lower level by sodium chloride solutions and by tubing manufactured from a variety of suitable materials (e.g., cyclic olefins, polyolefin, high density polyethylene, TPX® polymethylpentene, and fluorinated ethylene propylene).

In one embodiment, the conduit 48 through which light from the light source 44 is passed is a length of tubing (particularly tubing for the flow of a replacement fluid), but it should be understood that the present disclosure is not limited to tubing, but may include any other light-transmissive fluid flow conduit or structure or vessel through which a fluid, such as a replacement fluid, may pass. For example, it is within the scope of the present disclosure for replacement fluid flowing through flow conduit comprising a rigid, non-tubular optical chamber to be analyzed by light from a light source according to the foregoing description. In particular, it may be advantageous to provide a conduit or cuvette having relatively flat or planar surfaces through which the light from the light source 44 passes into and out of the conduit. By providing flat or planar surfaces instead of curved surfaces for the passage of light, the effect of adverse optical effects may be reduced, thereby improving the accuracy of the citrate detector 42.

Accordingly, in one embodiment, the light source 44 is an ultraviolet light source configured to emit light including a wavelength between approximately 200 and approximately 250 nm. If the light source 44 is configured to emit light having a broader band of wavelengths than what is absorbed by citrate (e.g., if a mercury vapor lamp is used as a light source), one or more filters 50 may be provided between the light source 44 and the light detector 46 to filter out any wavelengths falling outside of the target or ideal range of values. The nature of filters 50, if provided, may vary without departing from the scope of the present disclosure. For example, in one embodiment, the citrate detector 42 may be provided with a band pass filter 50, a broad band filter 50*a*, and an ultraviolet band pass filter 50*b*.

The light detector 46 is configured to receive the light emitted by the light source 44. Thus, if the light source 44 comprises an ultraviolet light source, the light detector 46 comprises an ultraviolet light detector. While the light detector 46 is active, it may send signals or data to the controller 30 of the system 10. Alternatively, the light detector 46 may send signals or data to an independent controller or processor. The controller or processor receives the signals or data and determines whether there is citrate present in the conduit 48 between the light source 44 and the light detector 46. If the controller or processor determines that there is citrate present in the conduit 48, it may generate an "error" output to alert the operator. This may be in any of a number of forms, such as an audible siren or alert, a message displayed on a video screen, or a combination of alerts. The output generated by the controller or processor may additionally serve to halt the operation of the system 10 (or at least selected components thereof) to prevent the infusion of sodium citrate to the blood source.

The manner in which the controller or processor determines the presence of citrate may be achieved in any of a variety of ways. In one embodiment, the controller or processor may determine or be provided with a baseline value that represents the amount of light received by the light detector 46 in the absence of citrate in the conduit 48. This determination of a baseline value may be carried out prior to fluid flow through the conduit 48. It may be advantageous for the controller or processor to determine a new baseline value for each procedure in the event that the amount of light emitted by the light source 44 decreases over time. The baseline value is compared to the signal(s) or data transmitted from the light detector 46 to the controller or processor while fluid is flowing through the conduit 48. If the signal(s) or data received by the controller or processor during fluid flow through the conduit 48 is equal to the baseline value, it is indicative of replacement fluid flowing through the conduit 48 (i.e., the absence of sodium citrate). In this case, the controller or processor may either generate no output or generate an "all clear" output that alerts the operator that the replacement fluid container has been properly connected to the disposable set 14. In one embodiment, such an output may be a prerequisite to the reinfusion of fluid to the blood source or other operations of the system 10. Alternatively, rather than requiring the signal(s) or data received by the controller or processor to be equal to the baseline value, it may be sufficient if the signal(s) or data is substantially or at least generally equal to the baseline value. For example, a preselected variation from the baseline value (e.g., a 5% deviation) may be allowed by the controller or processor when generating an "all clear" output.

On the other hand, if the signal(s) or data received by the controller or processor during fluid flow through the conduit 48 is not equal to the baseline value (on account of light being absorbed before reaching the light detector 46), it may be indicative of sodium citrate flowing through the conduit 48. The variation from the baseline value that triggers an "error" output may vary in different embodiments. For example, in some embodiments, an "error" output will not be generated by the controller or processor unless the received signal(s) or data is less than 50% of the baseline value, while in other embodiments an "error" output may be generated by a greater or lesser variation from the baseline value. In some embodiments, beyond simply determining whether citrate is present in the conduit 48, the controller or processor may determine the amount or concentration of citrate in the conduit 48. This may be achieved in any of a variety of ways, but may be based on the magnitude of the variation from the baseline value, which may correspond generally to the amount or concentration of citrate in the conduit 48 (i.e., a greater variation from the baseline value is indicative of a greater amount or concentration of citrate).

In addition to the aforementioned two outputs that may be generated by the controller or processor (i.e., an "error" output that is indicative of the presence of sodium citrate and an "all clear" output that is indicative of the absence of sodium citrate in the conduit 48), additional outputs may also be generated by the controller or processor. For example, the controller or processor may be programmed such that, if the signal(s) or data received by the controller or processor is not equal to the baseline value (or is greater than the preselected allowable variation from the baseline value), but less than the variation required to generate an "error" output, the controller or processor will generate a third output. This third output may be in the form of an alert for the system operator to check the containers 18 to ensure that the replacement fluid container is connected to the proper tubing or conduit 48. The controller may also be programmed to convert the variation data to a calculated concentration of citrate and display the concentration, if desired.

In addition to the light source 44 and light detector 46, the citrate detector 42 may include a variety of other components without departing from the scope of the present disclosure. For example, in the illustrated embodiment, the citrate detector 42 includes a heat-reducing shield or cover or member 52 adjacent to the light source 44, three filters 50-50b positioned between the light source 44 and the light detector 46, and a light-absorbing shield or cover or member 54 adjacent to the conduit 48. The heat-reducing member 52, if provided, controls heat exchange between the light source 44 and the system 10 or surrounding environment. Additionally, the wavelength of light emitted by some light sources may vary over time as the light source is in operation and heats up, in which case the heat-reducing member 52 may comprise a fan or heat sink or the like to help maintain the light source 44 at a lower temperature during use. In practice, it may be preferable for the light source 44 to be operated for only a short time during each processing cycle (e.g., only long enough to determine the content of the fluid in the conduit 48), rather than being operable during the entire cycle to reduce the risk of heat affecting the performance of the light source 44.

The filters 50-50b, if provided, condition the light passing from the light source 44 to the light detector 46 (e.g., by filtering out certain wavelengths), as described above in greater detail. The light-absorbing member 54, if provided, prevents extraneous light from the environment from being transmitted to the light detector 46 and may prevent the release of light from the light source 44 into the surrounding environment. For example, if the light source 44 is an ultraviolet light source, it may be advantageous for the light-absorbing member 54 to absorb ultraviolet light to prevent ultraviolet environmental light from reaching the light detector 46, which could affect the performance of the citrate detector 42.

Figure 6:
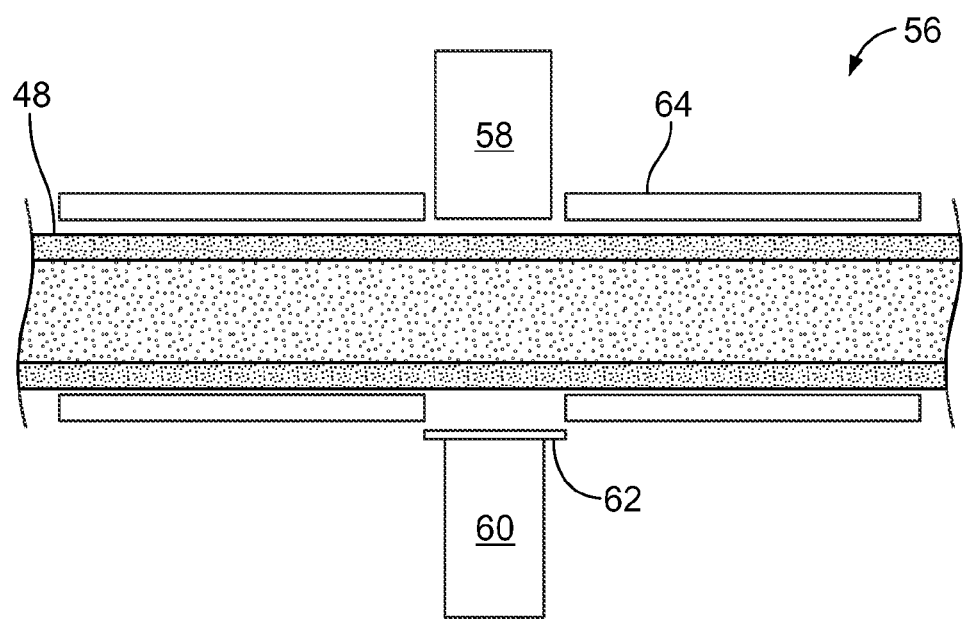
FIG. 6 is a diagrammatic view of a fluid detector that may be used in combination with the citrate detector of FIG. 5.

The citrate detector 42 may be employed alone or in combination with a flow detector 56 (FIG. 6). If provided, the flow detector 56 determines whether there is fluid present in the conduit 48. The detectors 42 and 56 may be associated with each other (e.g., via the controller or processor), such that the operation of the citrate detector 42 is dependent upon the presence of fluid in the conduit 48 and will not be actuated until the flow detector 56 generates a signal or data to indicate that there is fluid flow through the conduit 48.

In one embodiment, the flow detector 56 includes a light source 58 (such as, but not limited to, one or more light-emitting diodes) and a light detector 60 (such as, but not limited to, a photodiode), with the light detector 60 being configured and oriented to receive light from the light source 58. The light source 58 and light detector 60 are spaced apart a sufficient distance to accommodate a portion of the replacement fluid conduit 48 therebetween. Preferably, the flow detector 56 is associated with a portion of the conduit 48 that is upstream of the citrate detector 42 to detect the presence of fluid flow through the conduit 48 before the fluid reaches the citrate detector 42.

The light source 58 emits a light having a wavelength that is absorbed by water or a water-based solution (e.g., saline or an anticoagulant containing sodium citrate), but not by the conduit 48. It has been found that infrared light is absorbed by water and water-based solutions, but at least partially transmitted by tubing or conduits manufactured from a variety of suitable materials. Accordingly, in one embodiment, the light source 58 is an infrared light source configured to emit light including a wavelength in the infrared range of values. If the light source 58 is configured to emit light having a broader band of wavelengths than what is absorbed by water and water-based solutions, one or more filters 62 may be provided between the light source 58 and the light detector 60 to filter out any wavelengths falling outside of the target or ideal range of values. In the illustrated embodiment, the flow detector 56 is shown with a band pass filter 62, but other types of filters may also be employed without departing from the scope of the present disclosure.

The light detector 60 is configured to receive the light emitted by the light source 58. Thus, if the light source 58 comprises an infrared light source, the light detector 60 comprises an infrared light detector. While the light detector 60 is active, it may send signals or data to the controller 30 of the system 10 or to an independent controller or processor. It may be advantageous for the citrate detector 42 and the flow detector 56 to be associated with the same controller or processor. The controller or processor receives the signals or data and determines whether there is fluid flow in the conduit 48 between the light source 58 and the light detector 60. If the controller or processor determines that there is fluid present in the conduit 48, it may generate an output, such as a command to actuate the citrate detector 42.

The manner in which the controller or processor determines the presence of fluid in the conduit 48 may be achieved in any of a variety of ways. In one embodiment, the controller or processor may determine or be provided with a baseline value (which is a second baseline value that is different from the baseline value described above with regard to the citrate detector 42) that represents the amount of light received by the light detector 60 in the absence of fluid in the conduit 48. The baseline value is compared to the signal(s) or data transmitted from the light detector 60 to the controller or processor. If the signal(s) or data received by the controller or processor is equal to the baseline value, it is indicative of the absence of fluid in the conduit 48. In this case, the controller or processor may forego generating an output to actuate the citrate detector 42. Alternatively, rather than requiring the signal(s) or data received by the controller or processor to be equal to the baseline value, it may be sufficient if the signal(s) or data is substantially or at least generally equal to the baseline value. For example, a preselected variation from the baseline value (e.g., a 5% deviation) may be allowed by the controller or processor in determining that there is no fluid in the conduit 48.

On the other hand, if the signal(s) or data received by the controller or processor during fluid flow through the conduit 48 is not equal to the baseline value (on account of light being absorbed before reaching the light detector 60), it may be indicative of fluid flowing through the conduit 48. The variation from the baseline value that triggers a "power on" output or command (which triggers operation of the citrate detector 42) may vary in different embodiments. For example, in some embodiments, a "power on" output will not be generated by the controller or processor unless the received signal(s) or data is less than 90% of the baseline value, while in other embodiments a "power on" output or command may be generated by a greater or lesser variation from the baseline value. The controller may be programmed to convert the variation data to a calculated concentration or amount of fluid and display the concentration or amount, if desired.

In addition to the light source 58 and light detector 60, the flow detector 56 may include a variety of other components without departing from the scope of the present disclosure. For example, in the illustrated embodiment, the flow detector 56 includes the aforementioned filter 62 and a light-absorbing shield or cover or member 64 adjacent to the conduit 48. The light-absorbing member 64 provides the same function for the flow detector 56 as the light-absorbing member 54 provides for the citrate detector 42. Additionally, the light-absorbing members 54 and 64 may serve to prevent light from one detector from reaching the light detector of the other detector (e.g., preventing light from the light source 44 of the citrate detector 42 from reaching the light detector 60 of the flow detector 56). To further prevent light interference between the two detectors 42 and 56, it may be advantageous for them be spaced apart along the length of the conduit 48.

Figure 7:
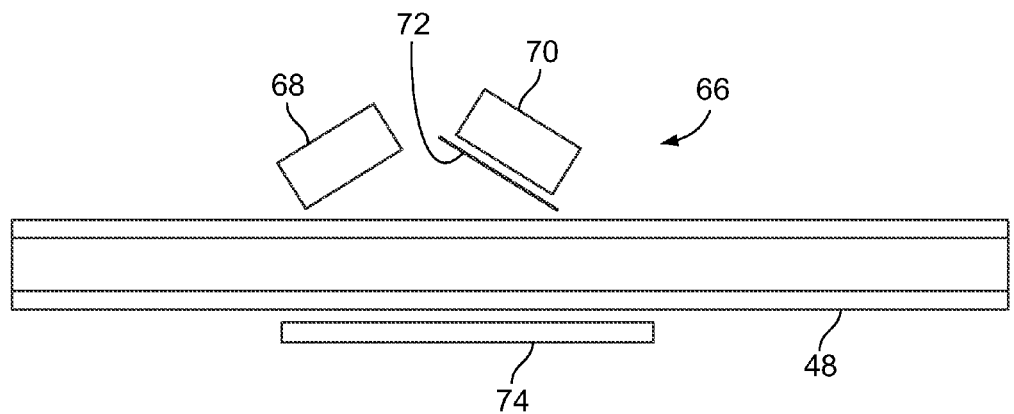
FIG. 7 is a side elevational view of an alternative embodiment of a citrate detector according to an aspect of the present disclosure.
Figure 8:
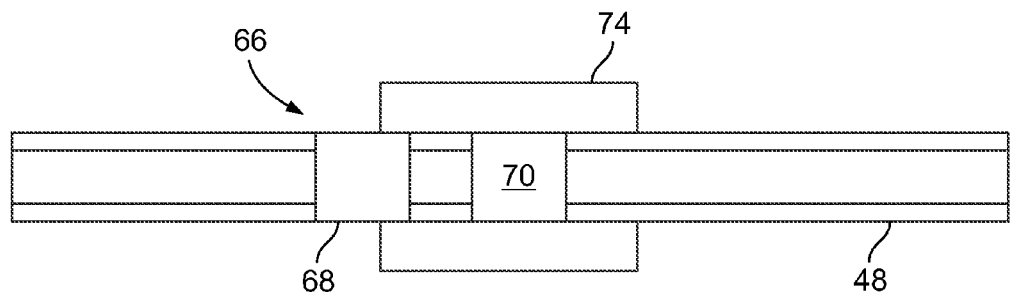
FIG. 8 is a top plan view of the citrate detector of FIG. 7.

In some embodiments, a flow detector 56 incorporating an infrared light source may be capable of detecting the presence of citrate or a citrate solution. In such circumstances, the flow detector 56 may replace the citrate detector and perform the detection duties of both a flow detector and a citrate detector. For example, FIGS. 7 and 8 show a citrate/flow detector 66 comprising an infrared light source 68 (e.g., a light-emitting diode or the like) and a light detector 70 (e.g., photodiode or the like) configured for receiving infrared light from the light source 68. While FIGS. 7 and 8 illustrate the light source 68 and the light detector 70 as being physically separate components, they may be integrated into a common detector housing or frame or the like.

In contrast to the citrate detector 42 of FIG. 5, the light source 68 and light detector 70 are not positioned generally opposite each other, with the conduit 48 positioned therebetween. It has been found that infrared light reflected from a citrate-containing fluid (as well as other organic solutions) produces peak measurements that are not produced in infrared light reflected from a substantially citrate-free fluid (e.g., saline), such that, in the illustrated embodiment the light detector 70 is positioned and oriented so as to receive light from the light detector 70 that has been reflected from the conduit 48 and the fluid flowing therethrough. For example, in one embodiment, there is a peak for light having a wave number of approximately 1574 $cm^{-1}$ (or a wavelength of approximately 6,353.24 nm) that can be detected using infrared subtraction techniques. At such a wavelength, PVC is effectively transparent, meaning that the conduit 48 may be comprised of PVC (e.g., flexible PVC tubing), but may also be comprised of any other suitable material(s).

In addition to the light source 68 and the light detector 70, additional components may be included. For example, FIGS. 7 and 8 illustrate a filter 72 and a reflector 74. The filter 72 is oriented to receive light prior to the light encountering the light detector 70, and more or fewer than one filter 72 may be provided. If provided, the filter 72 may be variously configured, but in one embodiment it comprises a band pass filter that is configured to filter out wavelengths that are different from the target wavelength (e.g., a target wavelength of approximately 6,353.24 nm). As for the reflector 74, it is oriented and configured to concentrate reflected light on the light detector 70. The illustrated reflector 74 is positioned opposite the light source 68 and the light detector 70, with the conduit 48 positioned therebetween, but the reflector 74 (if provided) may be placed at other locations without departing from the scope of the present disclosure. The reflector 74 may be variously configured, but in one embodiment comprises a mirror or a similar surface with light-reflective properties. More or fewer than one reflector 74 may be provided, and if multiple reflectors 74 are provided, they may be similarly or differently configured without departing from the scope of the present disclosure.

It is also within the scope of the present disclosure for a flow detector to be used in combination with a separate citrate detector, in which case the citrate-detection functionality of the flow detector may be used as a back-up to the dedicated citrate detector, to decrease the risk of malfunction or failure. In other embodiments, the citrate detector itself may incorporate an infrared light source (as in FIGS. 7 and 8) to detect the presence of citrate or a citrate solution. Furthermore, if a fluid being monitored by a detector having an infrared light source includes a plurality of components having specific characteristic infrared absorption properties, it may be possible to measure these values and determine the composition of the fluid based at least in part on the measurements.

Aspects of the present subject matter described above may be beneficial alone or in combination with one or more other aspects. Without limiting the foregoing description, in accordance with one aspect of the subject matter herein, there is provided a citrate detector for use in combination with a blood processing system and a replacement fluid flow conduit of a disposable set. The citrate detector includes a light source configured to emit a light having a wavelength absorbed by citrate, but at least partially transmitted by the replacement fluid flow conduit of the disposable set. The citrate detector also includes a light detector configured to receive at least a portion of the light from the light source and generate a signal indicative of the presence or absence of citrate in the replacement fluid flow conduit based, at least in part, on the amount of light received from the light source.

In accordance with another aspect which may be used or combined with the preceding aspect, the light source is configured to emit an ultraviolet light.

In accordance with another aspect which may be used or combined with any of the preceding aspects, a light-absorbing member configured to absorb ultraviolet light is provided adjacent to the light source.

In accordance with another aspect which may be used or combined with any of the preceding aspects, the light source is configured to emit ultraviolet light having a wavelength in the range of approximately 200 nm and approximately 250 nm.

In accordance with another aspect which may be used or combined with the preceding aspect, a filter configured to filter out wavelengths of light outside of the range is provided.

In accordance with another aspect which may be used or combined with the first aspect, the light source is configured to emit an infrared light.

In accordance with another aspect which may be used or combined with the preceding aspect, the light source is configured to emit infrared light having a wavelength of approximately 6,353.24 nm.

In accordance with another aspect which may be used or combined with any of the preceding two aspects, a reflector is configured to focus reflected light on the light detector.

In accordance with another aspect which may be used or combined with any of the preceding aspects, the light source is a light-emitting diode.

In accordance with another aspect, there is provided a blood processing system for use in combination with a replacement fluid flow conduit of a disposable set. The system includes a citrate detector and a controller. The citrate detector includes a light source configured to emit a light having a wavelength absorbed by citrate, but at least partially transmitted by the replacement fluid flow conduit of the disposable set. The citrate detector also includes a light detector configured to receive at least a portion of the light from the light source and generate a signal indicative of the presence or absence of citrate in the replacement fluid flow conduit based, at least in part, on the amount of light received from the light source. The controller is configured to receive the signal from the light detector and determine whether citrate is present in the replacement fluid flow conduit based, at least in part, on the signal.

In accordance with another aspect which may be used or combined with the preceding aspect, the light source is configured to emit an ultraviolet light.

In accordance with another aspect which may be used or combined with any of the preceding two aspects, a light-absorbing member configured to absorb ultraviolet light is provided adjacent to the light source.

In accordance with another aspect which may be used or combined with any of the preceding three aspects, the light source is configured to emit ultraviolet light having a wavelength in the range of approximately 200 nm and approximately 250 nm.

In accordance with another aspect which may be used or combined with the preceding aspect, a filter configured to filter out wavelengths of light outside of the range is provided.

In accordance with another aspect which may be used or combined with the tenth aspect, the light source is configured to emit an infrared light.

In accordance with another aspect which may be used or combined with the preceding aspect, the light source is configured to emit infrared light having a wavelength of approximately 6,353.24 nm.

In accordance with another aspect which may be used or combined with any of the preceding two aspects, a reflector is configured to focus reflected light on the light detector.

In accordance with another aspect which may be used or combined with any of the preceding eight aspects, the light source is a light-emitting diode.

In accordance with another aspect which may be used or combined with any of the preceding nine aspects, the controller is configured to compare the signal to a baseline value to determine whether citrate is present in the replacement fluid flow conduit.

In accordance with another aspect which may be used or combined with the preceding aspect, the controller is configured to generate an error output if the signal varies from the baseline value by more than a preselected amount.

In accordance with another aspect which may be used or combined with any of the preceding two aspects, the controller is configured to generate no output if the signal varies from the baseline value by less than a preselected amount.

In accordance with another aspect which may be used or combined with any of the preceding twelve aspects, a flow detector configured to determine the presence of fluid in the replacement fluid flow conduit is provided.

In accordance with another aspect which may be used or combined with the preceding aspect, the flow detector includes a light source and a light detector. The flow detector light source is configured to emit a light having a wavelength absorbed by water or a water-based solution, but at least partially transmitted by the replacement fluid flow conduit of the disposable set. The a flow detector light detector is configured to receive at least a portion of the light from the flow detector light source and generate a signal indicative of the presence or absence of fluid in the replacement fluid flow conduit.

In accordance with another aspect which may be used or combined with the preceding aspect, the flow detector light detector is associated with the controller. The controller is configured to receive the signal generated by the flow detector light detector and determine whether fluid is present in the replacement fluid flow conduit based, at least in part, on the signal from the flow detector light source.

In accordance with another aspect which may be used or combined with the preceding aspect, the controller is configured to compare the signal from the flow detector light detector to a second baseline value to determine whether fluid is present in the replacement fluid flow conduit.

In accordance with another aspect which may be used or combined with the preceding aspect, the controller is configured to generate an output that actuates the citrate detector if the signal from the flow detector light detector varies from the second baseline value by more than a preselected amount.

In accordance with another aspect which may be used or combined with any of the preceding four aspects, the flow detector light source is configured to emit an infrared light.

In accordance with another aspect which may be used or combined with any of the preceding five aspects, the flow detector light source is a light-emitting diode.

In accordance with another aspect, there is provided a method of monitoring fluid within a blood processing system having a replacement fluid flow conduit. The method includes directing light into the replacement fluid flow conduit, the light having a wavelength absorbed by citrate, but at least partially transmitted by the replacement fluid flow conduit.

The light exiting the replacement fluid flow conduit is detected, and it is determined whether citrate is present in the replacement fluid flow conduit based, at least in part, on the light exiting or reflected by the replacement fluid flow conduit.

In accordance with another aspect which may be used or combined with the preceding aspect, ultraviolet light is emitted into the replacement fluid flow conduit.

In accordance with another aspect which may be used or combined with any of the preceding two aspects, ultraviolet light having a wavelength in the range of approximately 200 nm and approximately 250 nm is emitted into the replacement fluid flow conduit.

In accordance with another aspect which may be used or combined with the preceding aspect, wavelengths of light outside of the range are filtered out.

In accordance with another aspect which may be used or combined with the twenty-ninth aspect, infrared light is emitted into the replacement fluid flow conduit.

In accordance with another aspect which may be used or combined with the preceding aspect, infrared light having a wavelength of approximately 6,353.24 nm is emitted into the replacement fluid flow conduit.

In accordance with another aspect which may be used or combined with any of the preceding six aspects, the amount of light exiting or reflected by the replacement fluid flow conduit is compared to a baseline value to determine whether citrate is present in the replacement fluid flow conduit.

In accordance with another aspect which may be used or combined with the preceding aspect, an error output is generated if the amount of light exiting or reflected by the replacement fluid flow conduit varies from the baseline value by more than a preselected amount.

In accordance with another aspect which may be used or combined with any of the preceding eight aspects, it is determined whether fluid is present in the replacement fluid flow conduit prior to emitting light into the replacement fluid flow conduit.

In accordance with another aspect which may be used or combined with the preceding aspect, the presence of fluid in the replacement fluid flow conduit is determined by emitting an infrared light into the replacement fluid flow conduit and analyzing the amount of infrared light exiting or reflected by the replacement fluid flow conduit.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A citrate detector for use in combination with a blood processing system and a replacement fluid flow conduit of a disposable set, the citrate detector comprising:
    a light source positioned and configured to emit a light onto the replacement fluid flow conduit of the disposable set and a fluid flowing through the replacement fluid flow conduit, the light having a wavelength absorbed by citrate, but at least partially transmitted by the replacement fluid flow conduit;
    a light detector positioned so as to receive at least a portion of the light from the light source that is exiting or reflected by the fluid in the replacement fluid flow conduit and generate a signal indicative of the presence or absence of citrate in the fluid in the replacement fluid flow conduit based, at least in part, on the amount of light received from the light source; and
    a flow detector configured to determine the presence of fluid in the replacement fluid flow conduit prior to the light source emitting light onto the replacement fluid flow conduit and the fluid flowing through the replacement fluid flow conduit.

2. The citrate detector of claim 1, wherein the light source is configured to emit an ultraviolet light.

3. The citrate detector of claim 2, wherein the light source is configured to emit ultraviolet light having a wavelength in the range of approximately 200 nm and approximately 250 nm.

4. The citrate detector of claim 1, further comprising a reflector configured to focus reflected light from the light source on the light detector.

5. The citrate detector of claim 1, wherein the light source comprises a light-emitting diode.

6. A blood processing system for use in combination with a replacement fluid flow conduit of a disposable set and comprising:
    a citrate detector including
        a light source positioned and configured to emit a light onto the replacement fluid flow conduit of the disposable set and a fluid flowing through the replacement fluid flow conduit, the light having a wavelength absorbed by citrate, but at least partially transmitted by the replacement fluid flow conduit,
        a light detector positioned so as to receive at least a portion of the light from the light source that is exiting or reflected by the fluid in the replacement fluid flow conduit and generate a signal indicative of the presence or absence of citrate in the replacement fluid flow conduit based, at least in part, on the amount of light received from the light source;
    a controller configured to receive the signal from the light detector and determine whether citrate is present in the fluid in the replacement fluid flow conduit based, at least in part, on the signal; and
    a light-absorbing member adjacent to the light source and configured to absorb ultraviolet light.

7. The blood processing system of claim 6, wherein the light source is configured to emit an ultraviolet light.

8. The blood processing system of claim 7, wherein the light source is configured to emit ultraviolet light having a wavelength in the range of approximately 200 nm and approximately 250 nm.

9. The blood processing system of claim 6, further comprising a reflector configured to focus reflected light from the light source on the light detector.

10. The blood processing system of claim 6, wherein the light source comprises a light-emitting diode.

11. The blood processing system of claim 6, wherein the controller is configured to compare the signal to a baseline value to determine whether citrate is present in the replacement fluid flow conduit.

12. The blood processing system of claim 6, further comprising a flow detector configured to determine the presence of fluid in the replacement fluid flow conduit prior to the light source emitting light onto the replacement fluid flow conduit and the fluid flowing through the replacement fluid flow conduit.

13. A method of monitoring fluid within a blood processing system having a replacement fluid flow conduit, the method comprising:

flowing a fluid through the replacement fluid flow conduit;
determining whether fluid is present in the replacement fluid flow conduit;
after determining that fluid is present in the replacement fluid flow conduit, directing light into the replacement fluid flow conduit, the light having a wavelength absorbed by citrate, but at least partially transmitted by the replacement fluid flow conduit;
detecting light exiting or reflected by the fluid in the replacement fluid flow conduit; and
determining whether citrate is present in the fluid in the replacement fluid flow conduit based, at least in part, on the light exiting or reflected by the fluid in the replacement fluid flow conduit.

14. The method of claim 13, wherein said emitting light into the replacement fluid flow conduit includes emitting ultraviolet light into the replacement fluid flow conduit.

15. The method of claim 13, wherein said emitting light into the replacement fluid flow conduit includes emitting ultraviolet light having a wavelength in the range of approximately 200 nm and approximately 250 nm into the replacement fluid flow conduit.

16. The method of claim 13, wherein said determining includes comparing the amount of light exiting or reflected by the fluid in the replacement fluid flow conduit to a baseline value.

17. The method of claim 13, wherein said directing light into the replacement fluid flow conduit includes directing light through a generally flat surface of the replacement fluid flow conduit.

18. The method of claim 13, wherein said directing light into the replacement fluid flow conduit and said detecting light exiting or reflected by the fluid in the replacement fluid flow conduit occurs on the same side of the replacement fluid flow conduit.

19. The method of claim 13, wherein said directing light into the replacement fluid flow conduit and said detecting light exiting or reflected by the fluid in the replacement fluid flow conduit occurs on opposite sides of the replacement fluid flow conduit.

20. A citrate detector for use in combination with a blood processing system and a replacement fluid flow conduit of a disposable set, the citrate detector comprising:

a light source positioned and configured to emit a light onto the replacement fluid flow conduit of the disposable set and a fluid flowing through the replacement fluid flow conduit, the light having a wavelength absorbed by citrate, but at least partially transmitted by the replacement fluid flow conduit;
a light detector positioned so as to receive at least a portion of the light from the light source that is exiting or reflected by the fluid in the replacement fluid flow conduit and generate a signal indicative of the presence or absence of citrate in the fluid in the replacement fluid flow conduit based, at least in part, on the amount of light received from the light source; and
a light-absorbing member adjacent to the light source and configured to absorb ultraviolet light.

21. A method of monitoring fluid within a blood processing system having a replacement fluid flow conduit, the method comprising:

flowing a fluid through the replacement fluid flow conduit;
directing light into the replacement fluid flow conduit, the light having a wavelength absorbed by citrate, but at least partially transmitted by the replacement fluid flow conduit;
detecting light exiting or reflected by the fluid in the replacement fluid flow conduit; and
determining whether citrate is present in the fluid in the replacement fluid flow conduit based, at least in part, on the light exiting or reflected by the fluid in the replacement fluid flow conduit, wherein said detecting light exiting or reflected by the fluid in the replacement fluid flow conduit includes absorbing environmental light prior to said environmental ultraviolet light being detected.

* * * * *